(12) United States Patent
Habets

(10) Patent No.: US 8,131,028 B2
(45) Date of Patent: Mar. 6, 2012

(54) METHOD AND APPARATUS PROVIDING FLEXIBLE MEASUREMENT FUNCTIONALITY FOR MEDICAL IMAGES

(75) Inventor: Raymond Joseph Elisabeth Habets, Eindhoven (NL)

(73) Assignee: Koninlijke Philips Electronics N.V., Eindhoven (NL)

( * ) Notice: Subject to any disclaimer, the term of this patent is extended or adjusted under 35 U.S.C. 154(b) by 393 days.

(21) Appl. No.: 10/597,146

(22) PCT Filed: Jan. 11, 2005

(86) PCT No.: PCT/IB2005/050114
§ 371 (c)(1), (2), (4) Date: Jul. 13, 2006

(87) PCT Pub. No.: WO2005/071527
PCT Pub. Date: Aug. 4, 2005

(65) Prior Publication Data
US 2008/0228061 A1    Sep. 18, 2008

(30) Foreign Application Priority Data
Jan. 19, 2004   (EP) ..................................... 04100149

(51) Int. Cl.
*G06K 9/00* (2006.01)
(52) U.S. Cl. ......... 382/128; 382/130; 382/131; 600/407
(58) Field of Classification Search .................. 382/128, 382/130, 132, 154, 131; 600/407; 345/157, 345/634, 619; 715/700
See application file for complete search history.

(56) References Cited

U.S. PATENT DOCUMENTS

| | | | | |
|---|---|---|---|---|
| 5,807,256 A | * | 9/1998 | Taguchi et al. | 600/425 |
| 6,272,366 B1 | * | 8/2001 | Vining | 600/407 |
| 6,366,800 B1 | * | 4/2002 | Vining et al. | 600/425 |
| 7,072,501 B2 | * | 7/2006 | Wood et al. | 382/132 |
| 7,453,472 B2 | * | 11/2008 | Goede et al. | 345/634 |
| 7,856,132 B2 | * | 12/2010 | Nijlunsing et al. | 382/131 |
| 2002/0067340 A1 | * | 6/2002 | Van Liere | 345/157 |
| 2003/0095697 A1 | * | 5/2003 | Wood et al. | 382/131 |

FOREIGN PATENT DOCUMENTS

EP    1349098    * 10/2003

* cited by examiner

*Primary Examiner* — Daniel Mariam
*Assistant Examiner* — Nancy Bitar

(57) ABSTRACT

In a medical imaging system the flexibility and power of measurement tools is improved by making the measurements objects themselves, whereby flexible interaction is provided. The measurement objects (52) are aware of their position relative to other graphical objects (50, 51), in the image. A user of a medical imaging system is thus enabled to easily perform desired measurements and to display the results thereof in a reliable and flexible manner. A method, an apparatus and a computer-readable medium are provided for processing cursored user interaction with a spatially displayed medical image for producing graphics related measurement data on the medical image. The medical image comprises at least one graphics object and dynamic measurement objects are attached to said graphics object, wherein the measurement object may be moved, removed or transferred to other graphic objects on the medical image at any time.

14 Claims, 5 Drawing Sheets

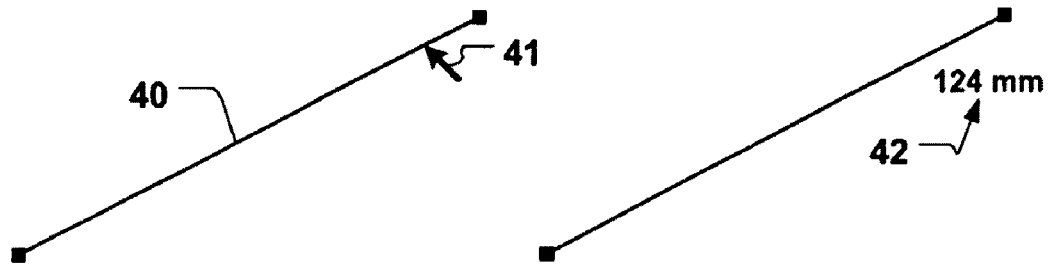
Fig. 4A　　　　Fig. 4B
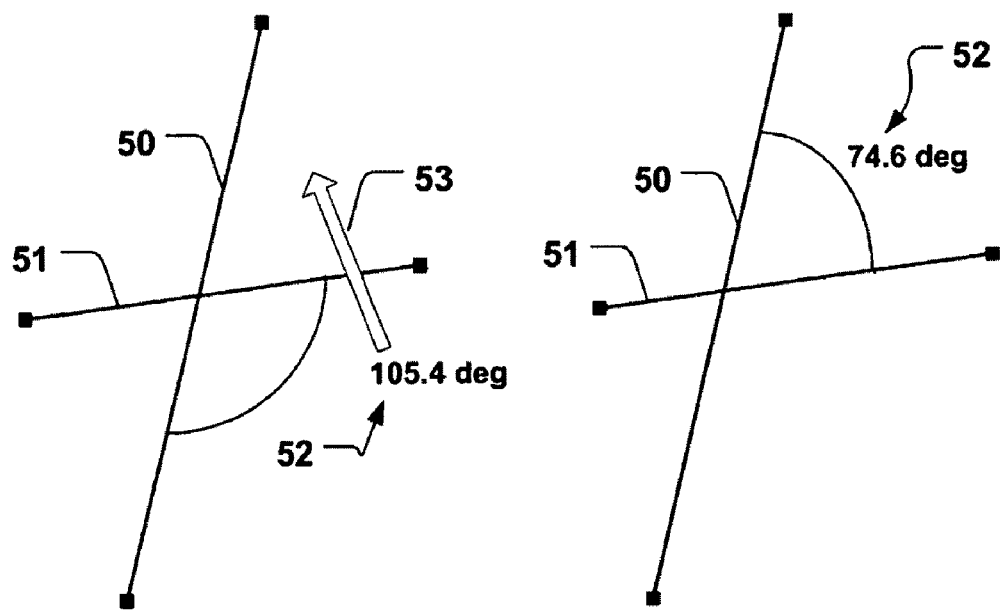
Fig. 5A　　　　Fig. 5B

METHOD AND APPARATUS PROVIDING FLEXIBLE MEASUREMENT FUNCTIONALITY FOR MEDICAL IMAGES

This invention pertains in general to the field of measurements related to images, and more particularly to the measurement of parameters in medical images, and even more particularly to the measurement of geometrical parameters, such as length and angles, related to objects being imaged on medical images.

Medical workstations and applications offer several standard measurement tools for measuring distances, such as lengths or diameters, and for measuring angles. For instance, specialists in the field of orthopaedics use medical software packages to measure physical properties of the skeletal system, such as the lengths of bones and angles between bone axes etc.

Distances are measured by drawing a line on an image, wherein the line is drawn between two points. A label near the line then displays the distance. Angles are measured by drawing two lines by means of three or four points on the image. A label displays the enclosed angle.

Such conventional measurements are for instance described in US-A-20020067340, wherein graphics objects are used for measurements. These graphics objects comprise the already mentioned lines and angles, which are constructed from a sequence of points or alternatively from drawn curves. A line is constructed from a point by adding a point, an angle is constructed from a line by adding a third point and a curve or contour is formed from the angle by entering an additional sequence of points. The resulting distance or angle is automatically displayed and respectively either attached to the line (distance) or shown enclosed between two lines (angle). A further example is given, wherein a user interactively constructs measuring tools starting with landmarks as basic building blocks. Subsequently an incremental graphics design approach is used for creating graphics objects and appertaining geometrical relational measurements.

However, these measurements according to the state of the art are static and it is not possible to interact with these measurements, except in some cases for moving the location of the measurement label. When angles are measured using two lines, it is very difficult to control which angle is intended, i.e. into which of the four quadrants the user intends to place the angular measurement. Moreover, for typical users of medical examination workstations, such as physicians, it is up to now not possible to add measurements to already existing graphic objects. Therefore, when a measurement is not satisfactory, it has either to be repeated in the above-described way, or it is not at all possible to accomplish a certain desired measurement.

Hence, there exists a need for "smart" measurement tools offering the user a wide range of flexibility in combination with ease of use.

The present invention overcomes the above-identified deficiencies in the art and solves at least the above-identified problems by providing a method, an apparatus and a computer-readable medium according to the appended patent claims.

The general solution according to the invention is to use measurements for which their position on the image determines the measurement to be performed.

More particularly, in order to provide the user with more control over what should actually be measured, measurement tools are made aware of the objects that they are measuring, of their position relative to these objects, and, in some cases, of their relative position on an image.

By means of the invention, the flexibility and power of measurement tools is increased by making them objects themselves that can be interacted with by the user and by making the objects aware of their position relative to other graphical objects in the image.

According to aspects of the invention, an apparatus, a method, and a computer-readable medium for smart measurements on medical images are disclosed.

According to one aspect of the invention, a method for processing user interaction in a medical environment with a medical image for producing measurement data related to graphics on the medical image is provided, wherein the graphics on the medical image comprises at least one graphic object and at least one dynamic measurement object based on said measurement data is removably attached to the at least one graphic object, i.e. the measurement object may be attached to graphics objects and then it may anytime be removed again or be transferred to another graphics object on the image.

According to another aspect of the invention, a medical examination apparatus adapted to implementing the above-mentioned method is provided. The apparatus comprises a cursor display means and user interaction means for a spatially displayed medical image on a graphics display means for displaying measurement data related to graphics objects on said image. Further, the apparatus comprises cursor actuating means with detection means for detecting positionings and actuations thereof, and measurement means for thereupon driving control of inherent measuring functionalities as being immediately based on graphics objects relative to the actuated position with respect to graphics objects having associated imaged medical objects.

According to a further aspect of the invention, a computer-readable medium having embodied thereon a computer program for processing by a computer of a medical examination apparatus is provided. The computer program comprises a plurality of code segments for processing by a processor for performing the above-mentioned method. A first code segment for processing user interaction in a medical environment with a medical image for producing measurement data related to graphics on the medical image, wherein the medical image comprises at least one graphic object. Furthermore, a second code segment is provided for removably attaching at least one dynamic measurement object to said graphic object.

The present invention has the advantage over the prior art that it enables a user of a medical imaging system to easily perform exact and accurate measurements more easily, and to display the results thereof in a reliable manner. Flexibility and power of measurement tools for medical images is improved by making the measurements objects themselves that can be interacted by the user, wherein these measurement objects also consider their position relative to the graphics objects they are connected to. The extraction of measurement information from a medical image is made significantly easier.

Further objects, features and advantages of the invention will become apparent from the following description of embodiments of the present invention, reference being made to the accompanying drawings, in which FIG. 1 is a schematic illustration of a medical imaging arrangement;

FIGS. 4A and 4B are schematic illustrations showing the creation of a length measurement object;

FIGS. 5A and 5B are schematic illustrations showing the principle of moving an angular measurement object between different quadrants of two intersecting lines;

Figure 1:
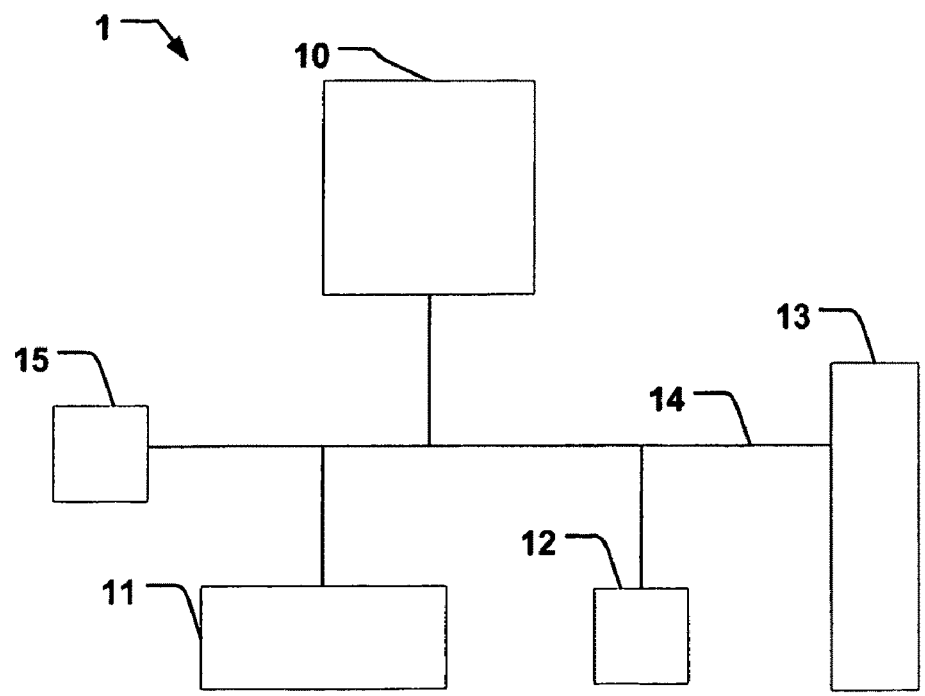

FIG. 1 shows an exemplary medical imaging system 1 as pertaining to one or more conventional imaging technologies, such as CT, MRI, or other. The system 1 comprises at least one image monitor 10, a keyboard 11, a mouse 12, and a processor provided with appropriate storage 13. All these subsystems are interconnected through a suitable interconnection facility 14 that can be bus-based. I/O facility 15 interconnects to an outer world for receiving image data derived from the detection subsystem not shown for brevity, and for outputting of processed image data for long-term storage, hardcopying, and other. A user person may manipulate a medical image, shown on monitor 10, in various manners, for instance as described in NL 031038 and US-A-20020067340, through mouse and/or keyboard actuations. Various other system configurations would be obvious to a person skilled in the art of image manipulating systems.

The present embodiment of method according to the invention is described hereinafter with reference to using simple mouse control in a system 1. Operation is foremostly controlled by a pointing device with at least one button, sometimes enhanced by accelerators and/or modifiers. The invention provides access to standard measurement operations, but does not rule out any particular measurement and may be adapted to specific requirements or specific measurements. The embodiment of the invention features the following non-limiting range of measurements: length, distance measurement diameter, perimeter, or alternatively such measurements in combination with pixel value profile measurements; angle measurements; as well as area, volume, grey value profiles (histogram), and other pixel value statistics measurements. These represent various operations on images without basically amending the image itself.

The system 1 implementing an embodiment of the invention is provided with a mouse for controlling operations. A mouse is provided in virtually all systems running viewing applications, as a mouse is a very cost-effective device. However, other devices such as graphics tablets, trackballs, force feedback joysticks, touch-screens or touch-pens are feasible as well and the present invention is not limited to a mouse as an input device. For controls such as touch screen and touch-pens there is actually no cursor. Cursors (or pointers) are necessary for position feedback if the user does not point directly to the screen like with a mouse. The pointer then is the only way to see where the mouse is. For touch screens and touch-pens the user physically points at the objects to select and thus cursor feedback is not necessary.

The embodiment of the method according to the invention uses graphics objects created by incremental graphics, wherein the graphics objects are associated with measurement objects according to the invention. The graphics objects are either manually created, or alternatively the graphics objects are automatically created, e.g. by image recognition software identifying imaged objects, such as bones or organs, in medical images. The graphics objects are e.g. a landmark (point), a single line with or without open ends, two lines, by contours delimited regions etc. One design principle of manually creating such graphics objects is discussed in US-A-20020067340. Another principle is discussed in NL 031038.

When using a mouse, generally two basic mouse interactions are possible: Click-Move-Click—the interaction is performed while no mouse button is pressed, or Press-Drag-Release—the interaction is performed while a mouse button is pressed. Of these, the click-move-click style has the advantage that the actual mouse motion is performed without a mouse button being pressed, such enabling a finer control. The press-drag-release style has the advantage that fewer mouse clicks are required. However, both styles may be used in connection with the invention.

In US-A-20020067340, all graphics measurement interactions are performed by moving a cursor to a position of interest on a medical image. Thereupon, a measurement object is activated for instance by clicking with a shift modifier. Then, optionally new positions can be added, and depending on the entered number of positions the measurement object changes from a point measurement (e.g. pixel value) to a line length measurement to an angle measurement to a polyline measurement (e.g. area).

Figure 2:
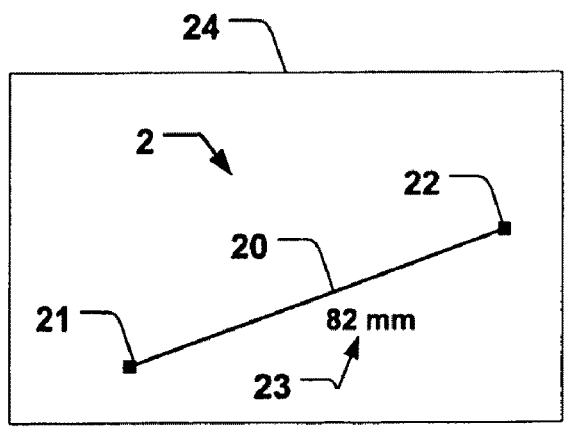
FIG. 2 is a schematic illustration of a line measurement principle according to the prior art.

FIG. 2 illustrates a prior-art line measurement principle 2 to measure distances between pairs 21, 22 of image points on a medical image 24. For images 24 with calibrated distance such as CT and MR images or explicitly calibrated RF images, the measurement value 23 displaying the length of the line 20 being drawn between the points 21 and 22 is displayed in a metric scale. In the example of FIG. 2 this value is 82 mm. For non-distance-calibrated images, the value is alternatively displayed in pixel co-ordinate units. The measurement value is automatically displayed at a fixed position nearby the line 20 when drawing the line 20 from point 21 to point 22 by means of a mouse. In US-A-20020067340 this procedure involves a plurality of steps:

1. Move cursor to the position of the first point 21 in image 24.
2. Click with a shift modifier to mark the first point 21 in the image, whereupon the pixel-value and position of point 21 are displayed.
3. Move cursor to the position of the second point 22. The pixel-value and position display are removed. A line pullout from the first point 21 to the cursor and the pullout distance is displayed. The line pullout and distance updated as cursor is moved.
4. Click to mark the second point 22 on image 24. The line pullout and pullout distance display are removed. The line 20 between the first 21 and second 22 points and the distance measurement 23 are displayed.
5. Click to finish the interaction.

Steps 3 and 4 are repeated for other graphics than lines, e.g. for angle graphics consisting of 3 or 4 points and two intersecting lines. An exemplary measurement of an angle between two intersecting lines according to NL 031038 will be discussed below in more detail with reference to FIG. 3.

The invention differs from this procedure. As illustrated in FIGS. 4A and 4B, a smart distance measurement object according to an embodiment of the invention docks to the selected line or set of points, or to the nearest line or set of points, i.e. all graphics objects that support a distance measurement. For illustrative purposes, the medical image underlying the measurements is not shown in the remainder of the description.

For the selection case the interaction is as follows:
1. Select the line or set of points
2a. Click the distance measurement button
or 2b. Click right and select a measurement (in this case distance) from the popup menu that presents all possible measurements with the current selection.

For the nearest case the interaction is as follows:
1. Move cursor to a line point position, i.e. a point on or adjacent to line 40; A cursor 41 is displayed.
2. Click e.g. with shift modifier to execute measurement or click right and select distance; Then the distance measurement object 42 is displayed as a measurement label near the line and interaction is finished. The position of measurement object 42 is either automatically adjusted in relation to the graphics object to which the measurement is connected, i.e. the line 40 of the example, or alternatively the measurement object 42 is positioned adjacent the graphics object at the position where the measurement object is activated by the clicking action. The latter is shown in FIG. 4B with relation to FIG. 4A, namely the measurement value of the measurement object is displayed as exemplary 124 mm.

Figure 7A:
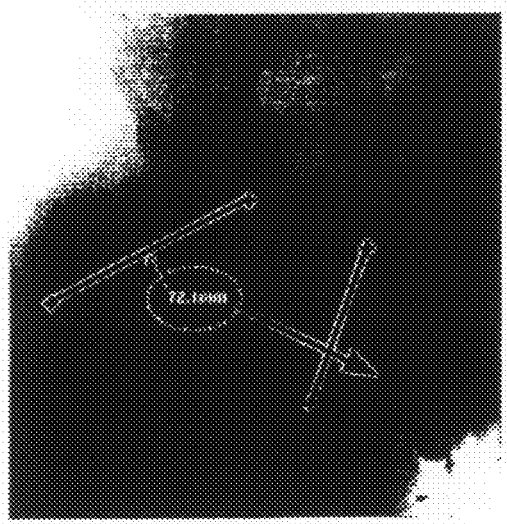
FIGS. 7A and 7B are medical images with graphical line objects illustrating the principle of moving a length measurement object.
Figure 7B:
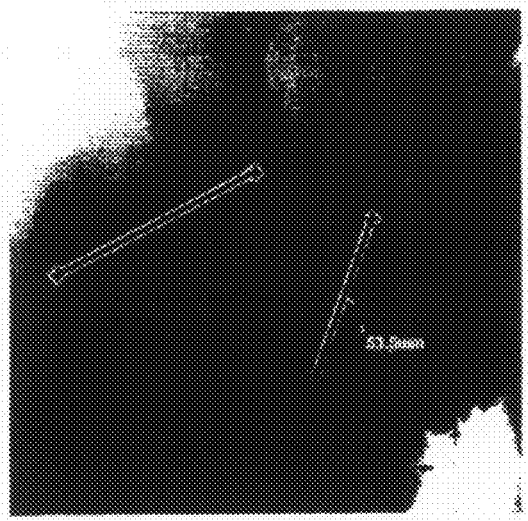

Another illustration that a smart distance measurement object docks to the nearest line or set of points, i.e. all graphics objects that support a distance measurement, is given in FIGS. 7A and 7B. FIGS. 7A and 7B are medical images with graphical line objects illustrating the principle of moving a length measurement object. The length measurement object shown in FIG. 7A that is connected to the left line is by means of cursored mouse interaction dragged to the right line, as indicated by the dotted circle line and the arrow in the Figure. FIG. 7B shows the situation after the drag. The length measurement object is switched from the first line (FIG. 7A) to the second line (FIG. 7B). Here it is further illustrated that the smart measurement objects of the invention are not simply labels showing the current measurement data of a fixed graphics object, as known from the prior art. The smart measurement objects are dynamically updated with the current measurement data of the graphics object that they currently are connected to. In the current example this is either the first or the second line. Of course two different smart measurement objects could also be connected to each line respectively.

The flexible measurement tool disclosed in NL031038 describes a user interface tooling to build measurement graphics in an incremental way. The 'smart measurement objects' of this present application may be used inside this flexible measurement tool. Instead of the static measurements, as e.g. disclosed in US-A-20020067340, i.e. static in the sense of their fixed connection to other graphic objects, the flexible measurement tool would then also comprise the smart measurement objects. The present invention may make use of the way in which the objects are created with a user interface for the 'selection' case, as described in NL031038. However, the 'nearest' case does not exist in NL031038. Smart objects may also be created initially unconnected, so that they are not incremental based on e.g. lines, and then the object may dock to the nearest graphic objects as soon as one exists that the smart measurement object can dock to. In case of a line, the static and the smart measurement end result look the same from a graphic point of view. However, the way of achieving this graphic is novel over the prior art and offers more flexibility to the user, when the measurement objects are to be modified from an existing state. This difference is well explained above in connection with FIG. 7.

Figure 3:
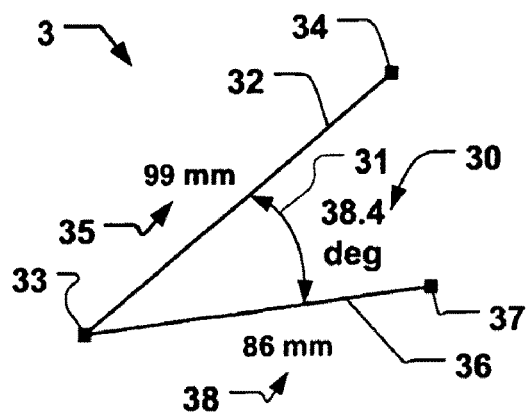
FIG. 3 is a schematic illustration of an angle value measurement principle according to the prior art.

FIG. 3 shows a prior art measurement principle 3 for measuring angle values 30 between connected pairs of lines 32, 36, and for distances between successive pairs of points on images. Calibrated images and images with known pixel aspect ratio have an angle value displayed in degrees. For instance in NL031038 the interaction is as follows: draw two landmarks 33, 34; select them; press the line button which creates a line 32; draw an additional landmark 37; select the two landmarks 33 and 37; press the line button which creates a second line 36; select both lines; press the angle button which creates an angle measurement 30,31; This fixed angle is defined as the sharp angle between the selected lines; select line 32; press the length button to add a linelength measurement 35 (99 mm); select the second line 36; press the length button again to add a linelength measurement 38 (86 mm) to the second line 36.

In contrast, FIGS. 5A and 5B are schematic illustrations showing the principle of moving an angular measurement object between different quadrants of two intersecting lines according to an embodiment of the invention.

A smart angle measurement object is positioned interactively with the mouse, or another control device, in one of the four quadrants formed by two lines. Depending on its position a different angle, and optionally a corresponding angle arc, will be displayed. Furthermore, the position of the displayed angle object, i.e. the position of the angle measurement value and the angle arc, if it exists, may be manually moved within the image by the operator in case these objects obstruct image parts, which are desired to be visible, wherein this moving action per se is already known, but not in combination with "smart" measurement objects. Thus, the smart angle measurement becomes an object itself, a flexible angle measurement object. The user picks up the label displaying the angle and places it in an appropriate position in one of the four quadrants formed by the intersecting lines. The angle measurement object displays then automatically the correct angle, at the desired position or at an automatically adjusted position, depending on user preferences.

The interaction to create a smart angle measurement is as follows:
1. Select two lines 50 and 51
2a. Click the angle measurement button
or 2b. Click right and select a measurement (in this case angle) from the popup menu that presents all possible measurements with the current selection; the angle measurement object 52 is displayed as an angle label in the selected quadrant and interaction is finished.

The move interaction with reference to FIGS. 5A and 5B is as follows: click on an existing smart angle measurement object 52 in the selected quadrant and drag object 52 to another quadrant of the same 50, 51, or a different set of intersecting lines as indicated by the arrow 53. Thus the user drags the angle label (105.4 deg) from the lower right quadrant to the upper right quadrant, and the angle measurement object comprising the label and the arc will change accordingly to the new measurement value of angle measurement object 52 in the upper right quadrant (74.6 deg) of the intersecting lines 50, 51, and interaction is finished.

In this respect, the angle, which the angle measurement object measures, depends on:
(1) the two lines (or other objects supporting an angle measurement) it is connected to and,
(2) its position on the image relative to the two objects it is connected to.

In the above example, the angle measurement object stays fixed to the two lines it is connected to. Alternatively the angle measurement object (via its label) may be dragged to a different set of two lines, for example the two lines nearest to the current location of the label, and then dock to these lines. Subsequently, the angle measurement object may be dragged to the desired quadrant of the current set of lines.

It is pointed out, that a measurement tool is defined as a graphic objects plus connected measurement objects, e.g. an entire angle measurement object. A measurement object is defined as the measurement plus the label.

Figures 8A, 8B:
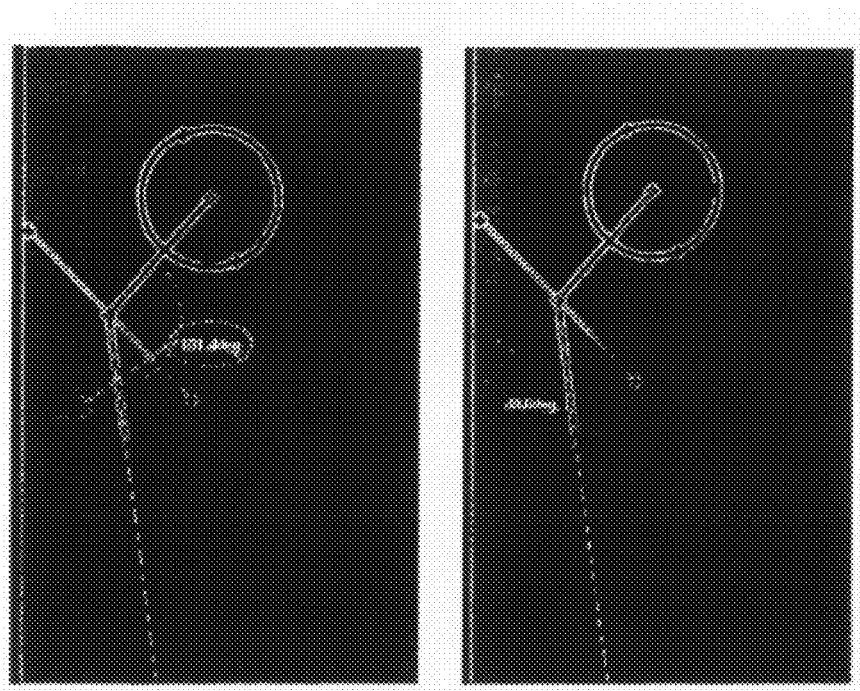
FIGS. 8A and 8B are medical images with graphical line objects illustrating a clinical example of moving an angular measurement object between different quadrants of two intersecting lines.

A clinical example of the smart angle measurement tool is shown in FIGS. 8A and 8B. The smart angle measurement object is illustrated in a clinically relevant situation. FIGS. 8A and 8B are medical images with graphical line objects illustrating a clinical example of moving an angular measurement object between different quadrants of two intersecting lines. More precisely, FIGS. 8A and 8B illustrate the measurement of the CCD angle, i.e. the angle between the femur anatomical axis and the femoral neck line. The Femur anatomical axis is the line from the midpoint of the two trochanter points, i.e. the two points connected by the dashed line, to the centre of the knee. The Femoral neck line is the line from the centre of the femoral head circle to the midpoint of the two trochanter points. The CCD angle is clinically defined as shown in FIG. 8A. If a user, such as a physician, wants to report the sharp angle instead, the angle measurement object is dragged to the wanted location. The result is shown in the FIG. 8B.

Figure 6A:
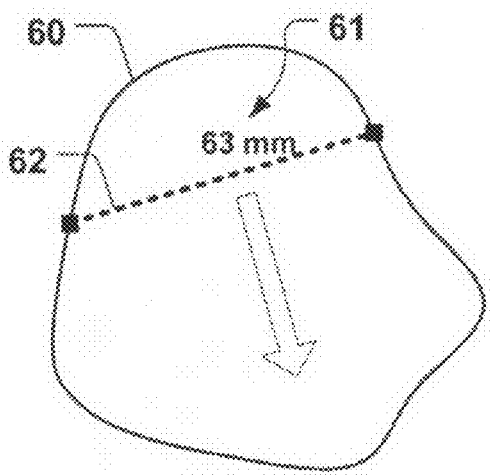
FIGS. 6A and 6B are schematic illustrations showing the movement of a dynamic length measurement of a diameter of a contour along the contour.
Figure 6B:
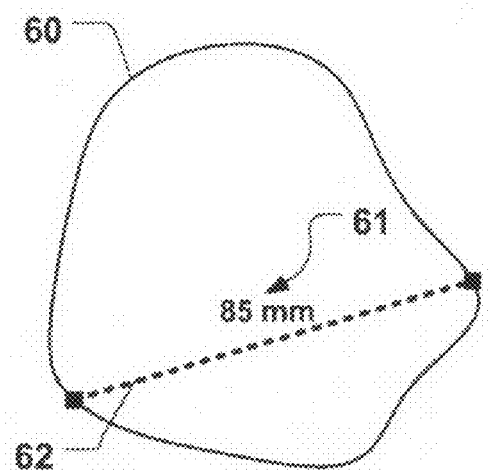

FIGS. 6A and 6B illustrate another implementation of the smart measurement tools according to the invention. FIGS. 6A and 6B are schematic illustrations showing the movement of a dynamic diameter measurement along a contour 60. A diameter measurement object 61 is shown. The diameter measurement object is visualised as a dotted line 62 between two points on the border of a contour 60. When the diameter measurement object is moved, as indicated by the arrow in FIG. 6A, its endpoints automatically snap to the nearest point on the closest contour. When the diameter measurement object line 62 is dragged downwards, its endpoints 'snap' to the border and the measurement updates, as illustrated in FIG. 6B. Alternatively, when the diameter measurement is dragged between two different contours, both endpoints will each 'snap' to a different contour, thus creating an inter-contour distance measurement. Optionally, the pixel-value profile of the image along the line may be displayed in a chart (not shown).

Copying of measurement tools, such as described above, is also possible. However in practice, it might be easier for the user to create a new measuring tool instead of copying it, depending on the user-friendliness of the current user interface.

Figure 9:
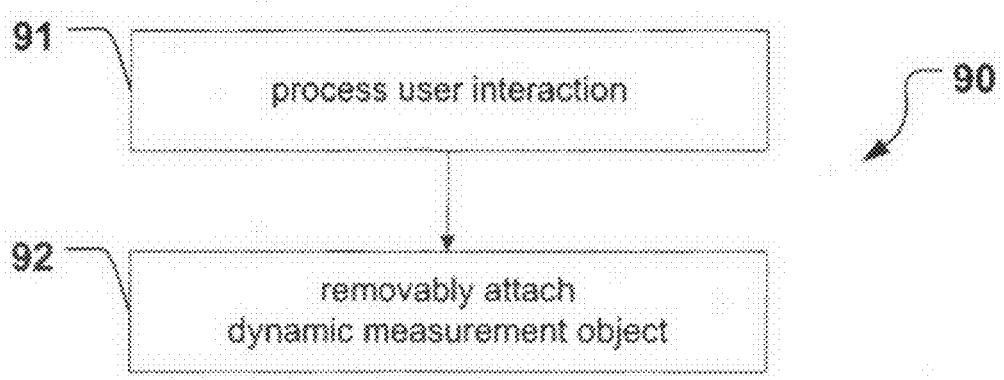
FIG. 9 is a schematic flow chart illustrating an embodiment of the method according to the invention.

FIG. 9 is a schematic flow chart illustrating an embodiment of the method according to the invention. FIG. 9 shows a method 90 of processing 91 cursored user interaction with a spatially displayed medical image for producing graphics related measurement data on the medical image. The medical image comprises at least one graphics object and dynamic measurement objects are removably attached 92 to at least one graphics object.

Figure 10:
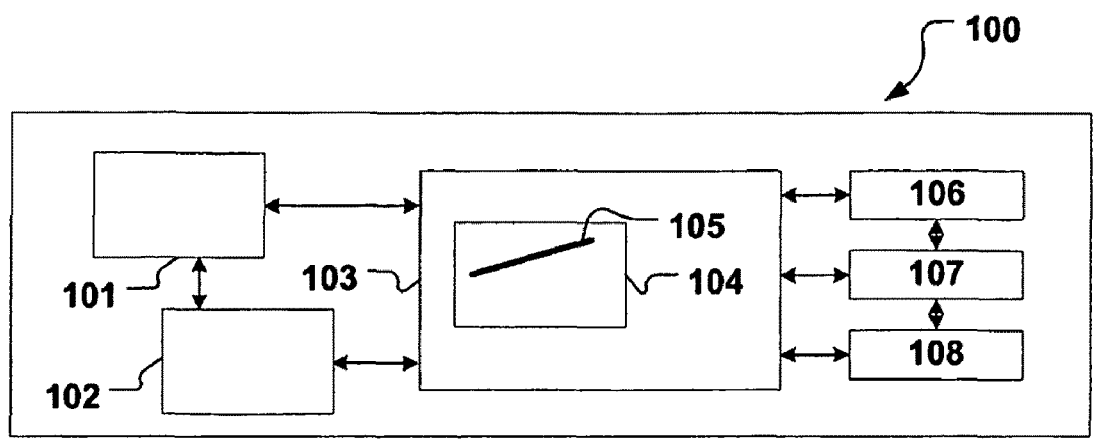
FIG. 10 is a schematic illustration of an embodiment of the apparatus according to the invention.

FIG. 10 is a schematic illustration of an embodiment of the apparatus according to the invention. The medical examination apparatus 100 is arranged for implementing the above-mentioned method according to the invention. The medical examination apparatus 100 is for example a CT acquisition apparatus, an MR acquisition apparatus, a conventional X-ray apparatus, or an other medical image acquisition apparatus. The medical examination apparatus 100 comprises computer readable memories 101, 102, 106, 107, and 108. The computer readable memory 101 comprises computer readable code designed to display a cursor. The computer readable memory 102 comprises computer readable code designed for user interaction with a spatially displayed medical image 104 on a graphics display like a Cathode Ray Tube monitor (CRT monitor) 103 for displaying measurement data related to graphics objects 105 on said image 104. Further, The computer readable memory 107 comprises computer readable code designed to store cursor actuations. The computer readable memory 106 comprises computer readable code designed to detect positionings and actuations based upon the stored cursor actuations. The computer readable memory 108 comprises computer readable code designed to thereupon driving control of inherent measuring functionalities as being immediately based on graphics objects 105 relative to the actuated position with respect to graphics objects having associated imaged medical objects. The computer readable memories communicate with a microprocessor through a software bus that is designed to transfer data from, to and between the memories, the microprocessor and the graphics display.

Figure 11:
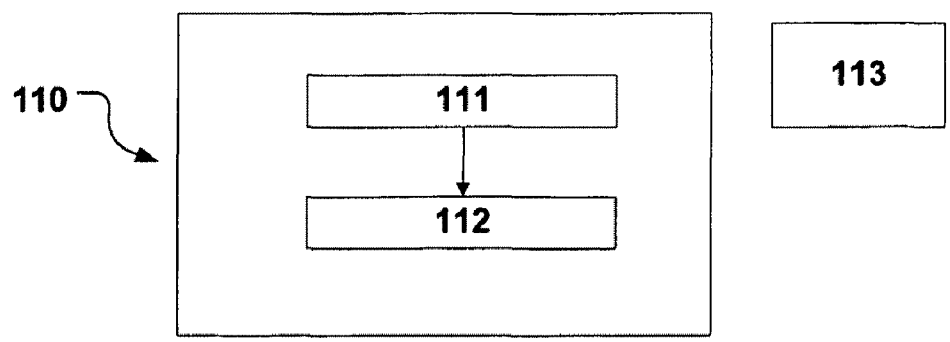
FIG. 11 is a schematic illustration of an embodiment of the computer-readable medium according to the invention.

FIG. 11 is a schematic illustration of an embodiment of the computer-readable medium according to the invention. The computer program 110 comprises a plurality of code segments 111, 112 for processing by a processor 113 performing the above-mentioned method, wherein a first code segment 111 is provided for processing user interaction in a medical environment with a medical image for producing measurement data related to graphics on the medical image, wherein the medical image comprises at least one graphic object, and a second code segment 112 for removably attaching at least one dynamic measurement objects to said graphic object.

Applications and use of the above described interactive measurements according to the invention are various and include for instance all medical viewing workstations, PACS systems, and all types of clinical applications. Moreover, the invention is suitable to be used in combination with images from all modalities.

The present invention has been described above with reference to specific embodiments. However, other embodiments than the preferred above are equally possible within the scope of the appended claims, e.g. different geometric measurements than those described above, performing the above method by hardware or software, etc. Measurement types that may benefit from docking 'in a smart way' are length, distance, diameter, perimeter, area, volume, grey value profiles (histogram), and more. A 'smart length' measurement object may dock to any graphical object in the image that supports measuring its length. A 'smart distance' measurement may dock to the two nearest objects supporting a distance measurement. A 'smart diameter' measurement may dock to contours, circles, spheres, tubes (like vessels, trachea . . . ) etc. Also, The system 1 implementing an embodiment of the invention is provided with a mouse for controlling operations. However, as mentioned above, other control devices for user-interaction with the system 1 may be used. This implies that for devices such as a touch screen or touch-pens, there actually is no need for a cursor and the cursor may be omitted in these cases. This is due to the fact that cursors (or pointers) are necessary for position feedback if the user does not point directly to the screen like with a mouse. The pointer then is the only way to see where user-interaction points the mouse on the display. For touch screens and touch-pens the user physically points at the objects to select and thus cursor feedback is not necessary.

Moreover, persons skilled in the art will recognize that the above disclosed method may be stored on a data carrier as a computer program that can effect of enhance an existing image processing machine to attain features of the present invention.

Furthermore, the term "comprises/comprising" when used in this specification does not exclude other elements or steps, the terms "a" and "an" do not exclude a plurality and a single processor or other units may fulfil the functions of several of the units or circuits recited in the claims.

The invention claimed is:

1. A method of processing user interaction in a medical environment with a medical image for producing measurement data related to graphics on the medical image, the method comprising:
    attaching a dynamic measurement object to a first graphic object displayed on a monitor, the dynamic measurement object including measurement data related to the first graphic object;
    detaching, via a user interface device, the dynamic measurement object from the first graphic object; and
    attaching, via the user interface device, the dynamic measurement object to a second graphic object displayed on the monitor, wherein the measurement data is modified to be related to the second graphic object.

2. The method according to claim 1, wherein the user interface device is cursor controlled and the medical image and first and second graphic object is displayed on the monitor of a medical examination apparatus.

3. The method according to claim 1, wherein the first and second graphic objects are associated with at least one anatomical structural element of medical objects on said medical image.

4. The method according to claim 1, wherein the measurement data is derived from the first and second graphic objects.

5. The method according to claim 4, wherein the first and second graphic objects are a point, a line, a curve, two intersecting lines, or a contour.

6. The method according to claim 4, wherein the measurement data that is derived from the first and second graphic objects is a line length, a curve length, an angle delimited by two intersecting lines, an area delimited by a contour or a profile along a line or a curve, a diameter, a perimeter, an area, a volume, or grey value profiles.

7. The method according to claim 1, wherein the attaching the dynamic measurement object to the first and second graphic objects, further comprises determining a nearest one of the first and second graphic objects supporting a specific measurement associated with the dynamic measurement object.

8. A medical examination apparatus being arranged for implementing the method of claim 1, said apparatus comprising cursor display means and user interaction means for a medical image displayed on a graphics display means for displaying measurement data related to graphics objects on said image, cursor actuating means with detection means for detecting positionings and actuations thereof, and measurement means for thereupon driving control of inherent measuring functionalities as being immediately based on graphics objects relative to the actuated position with respect to graphics objects having associated imaged medical objects.

9. Use of a medical examination apparatus according to claim 1 for processing user interaction in a medical environment with a medical image for producing measurement data related to graphics on the medical image, wherein the graphics on said medical image comprises at least one graphic objects, comprising removably attaching at least one dynamic measurement object to said graphic object in such a manner that the measurement object when attached to said graphic object is, upon further user interaction, removable from said graphic object, transferable along said graphic object or to another position adjacent to said graphic object, or transferable to different graphic objects on said medical image.

10. A computer-readable medium (110) having embodied thereon a computer program for processing by a computer (113) of a medical examination apparatus, the computer program comprising code segments for performing the method of claim 1, wherein the computer program comprises
    a first code segment (111) for processing user interaction in a medical environment with a medical image for producing measurement data related to graphics on the medical image, wherein the medical image comprises at least one graphic object, and
    a second code segment (112) for removably attaching at least one dynamic measurement object based on said measurement data to said graphic object.

11. The method according to claim 1, wherein the first and second graphic objects include two intersecting lines and the dynamic measurement object attached in a first quadrant between the two intersecting lines, the measurement data being an angle between the two intersecting lines in the first quadrant, the dynamic measurement object then being detached from the first quadrant and attached in a second quadrant between the two intersecting lines, the measurement data being a further angle between the two intersecting lines in the second quadrant.

12. The method according to claim 1, wherein the first and second graphic objects are contour curves.

13. The method according to claim 12, wherein the measurement data included in the dynamic measurement object is a length of the contour curves.

14. The method according to claim 12, wherein the measurement data included in the dynamic measurement object is a length of a line between a first point on the contour curve and a second point on the contour curves.

* * * * *